United States Patent [19]

Shibata

[11] Patent Number: 5,074,789
[45] Date of Patent: Dec. 24, 1991

[54] CHUCKING DEVICE FOR DENTAL HANDPIECE

[75] Inventor: Yuichi Shibata, Kanuma, Japan

[73] Assignee: Nakanishi Dental Mfg. Co., Ltd., Tochigi, Japan

[21] Appl. No.: 586,434

[22] Filed: Sep. 21, 1990

[30] Foreign Application Priority Data

Sep. 26, 1989 [JP] Japan ............................ 1-112170[U]

[51] Int. Cl.$^5$ ........................ A61C 1/08; A61C 1/14
[52] U.S. Cl. ................................ 433/129; 433/126; 433/127
[58] Field of Search ................... 433/127, 129, 126

[56] References Cited

U.S. PATENT DOCUMENTS

| | | | |
|---|---|---|---|
| 3,798,776 | 3/1974 | Lentine et al. | 433/129 |
| 3,869,796 | 3/1975 | Thorburn | 433/129 |
| 4,406,470 | 9/1983 | Kataoka et al. | 433/127 |
| 4,493,645 | 1/1985 | Nakanishi | 433/127 |
| 4,874,314 | 10/1989 | Fleer et al. | 433/129 |

Primary Examiner—John J. Wilson
Assistant Examiner—Cindy A. Cherichetti
Attorney, Agent, or Firm—Charles E. Baxley

[57] ABSTRACT

A chucking device for a dental handpiece includes a cutting tool, a collet having a plurality of slits to permit the cutting tool to be received and attached in position in the collet, a rotational sleeve for transmitting rotation to the collet, a locking member adapted to permit the diameter of the collet to be changed, and a coil spring thrusting the locking member along the inserting direction of the cutting tool. The outer periphery of the collet has a tapered surface adapted to be enlarged in diameter along the inserting direction of the cutting tool. The locking member is shifted along the tapered surface under the thrusting force of the coil spring to change the diameter of the collet to hold the cutting tool therein. When the locking member is pressed down against the coil spring, the locking member is then moved along the tapered surface in a direction opposite to the inserting direction of the cutting tool to release the cutting tool to permit the tool to be detached from the collet. If a tapered surface flared in the tool releasing direction is provided on the inner periphery of the collet, a tapered surface is formed on the outer periphery of the collet on insertion of the cutting tool to provide the similar function.

11 Claims, 3 Drawing Sheets 5,074,789

CHUCKING DEVICE FOR DENTAL HANDPIECE

BACKGROUND OF THE INVENTION

This invention relates to a chucking device for a dental handpiece.

Up to now, a dental handpiece fitted with a cutting tool or bur has been used extensively for dental treatment This dental handpiece is provided therein with a driving member operated by pneumatic pressure or electrical power, a water feed conduit and air supplying and discharging conduits. The driving member is adapted for rotating the cutting tool or bur carrying a grinding end. In dental treatment, the cutting tool having the grinding end of the desired shape or size is selected as a function of the position or size of the site under treatment and attached to the tool head in exchange for a previously used tool.

FIG. 5 shows a tool head 1 of a conventional dental handpiece. The tool head 1 is constituted by a head housing 3 for attachment of a dental tool, such as a cutting tool 23, and a head housing jacket 2. A rotational sleeve 15 rotated by a rotor 15a and adapted for rotating a collet 10 as later described is mounted at the center of the head housing 3. Upper and lower ball bearins 5, 6 are accommodated within an inner casing 4. A cartridge cover 8 for the inner casing 4 is fitted to the upper end of the inner casing 4. Dampers 7 and 9 are provided between the cartridge cover 8 and the ball bearing 5 and between the ball bearing 6 and the inner casing 4, respectively, for taking up the vibrations produced by rotation of the rotational sleeve 15.

The aforementioned collet 10 having a plurality of vertically extending slits 11 is slidably accommodated within the rotational sleeve 15 for receiving and securing the cutting tool 23. The outer periphery of the lower end of the collet 10 has a tapered surface 12 which is flared towards below, while the upper end of the collet 10 is threaded and engaged by a mating set screw 13 having a flange 14. A coil spring 18 is interposed between the flange 14 and the upper end of the rotational sleeve 15 for perpetually biasing the collet 10 upwards with respect to the rotational sleeve 15. A step 16 is formed on the inner periphery of the rotational sleeve 15 for perpetually engaging with a corresponding step at the lower end of the tapered surface 12. Thus, the tapered surface 12 is pressed by the sleeve 15 and retained at the step 16, the tapered portion of the collet 10 being contracted in diameter.

A coil spring retainer 19 having a central collet insertion opening 20 is threadedly engaged with an upper central opening of the head housing 3 and a pushbutton 21 for retention and releasing of the cutting tool 23 by a one-touch operation is provided in the upper end opening of the coil spring retainer 19 so as to be perpetually biased upwards by a coil spring 22.

With the above construction of the dental handpiece, when attaching the cutting tool 23 to the tool head 1, the upper end of the cutting tool 23 is pushed into the inside of the tubular collet 10 by way of a cutting tool insertion tube 17, while the pushbutton 21 is pushed by finger pressure. At this time, under the thrusting pressure of the cutting tool 23, the collet 10 is enlarged in diameter due to extension at the slits 11 to accommodate the cutting tool 23. When the finger pressure on the pushbutton 21 is released, since the collet 10 is biased upwards by the coil spring 18 by means of the flange 14 of the set screw 13, the tapered surface 12 of the collet 10 is compressed radially inwardly so that the collet 10 holds the cutting tool 23 in position under the radially compressive force exerted by the tapered surface 12.

For extracting the cutting tool 23 from the collet 10, the pushbutton 21 is pushed down by application of a finger pressure against the force of the coil spring 22. This causes the set screw 13 to be lowered against the action of the coil spring 18, while causing the collect 10 to be lowered with respect to the rotational sleeve 15 to release the radial pressure exerted by the tapered surface 12 on the tool 23 so as to release the holding of the cutting tool 23 by the tapered surface 12 to thus permit facilitated exchange of the cutting tool 23.

With the above described conventional dental hanpiece, when a force in the tool releasing direction, i.e. in the downward direction in FIG. 5, is applied to the cutting tool 23, the tool 23 is moved downwards with respect to the rotational sleeve 15, leading to entraining the collet 10 in such downward movement At this time, the tapered surface 12 is flared downwards along the direction opposite to the tool inserting direction, that is in the releasing direction of the tool 23, so that, when the collet 10 is moved in this manner with respect to the rotational sleeve 15, the radially compressive holding pressure applied by the tapered surface 12 of the collet 10 against the rotational sleeve 15 is diminished. This tendency becomes more pronounced as the amount of downward movement of the collet 10 is increased, so that the tool 23 tends to be extracted when a force in the releasing direction is applied to the tool 23.

SUMMARY OF THE INVENTION

It is a principal object of the present invention to provide a chucking device for a dental handpiece in which the dental tool may be held strongly even when a force in the tool releasing direction is applied to the dental tool, so that the tool may be prevented from being extracted accidentally from the collet It is another object of the present invention to provide a chucking device for a dental handpiece in which the dental tool may be held and released promptly by a one-touch operation.

The above and other objects of the present invention will become more apparent from the following description.

In accordance with the present invention, there is provided a chucking device for a dental handpiece comprising a dental tool for performing dental treatment, a collet for accommodating the dental tool therein and having a plurality of slits allowing the diameter of the collet to be changed to hold or release the tool, the collet having a tapered surface, a rotational sleeve accommodating the collet therein and adapted for transmitting rotation to the collet to permit dental treatment, a locking member adapted for being contacted with the tapered surface of the collet for contracting the collet in diameter to hold the dental tool in the collet and thrusting means for thrusting the locking member along the inserting direction of the dental tool, wherein, the collet has a tapered surface flared along the inserting direction of the dental tool so that during the operation of attaching the dental tool in position, the locking member thrust by the thrusting means is moved along the tapered surface of the collet along the inserting direction of the tool to contract the collet in diameter to hold the tool in the collet against acciental extraction thereof, and wherein, during the operation of exchanging the dental tool, the locking member is thrust against the thrusting force of the thrusting means to shift the locking member along the tapered surface of the collet in a direction opposite to the inserting direction of the tool to release the holding of the tool by the collet to thus release the dental tool out of the collet.

BRIEF DESCRIPTION OF THE DRAWINGS

FIG. 4b is a cross-sectional view taken along line IVb—IVb of FIG. 4a;

PREFERRED EMBODIMENTS OF THE INVENTION

Figure 5:
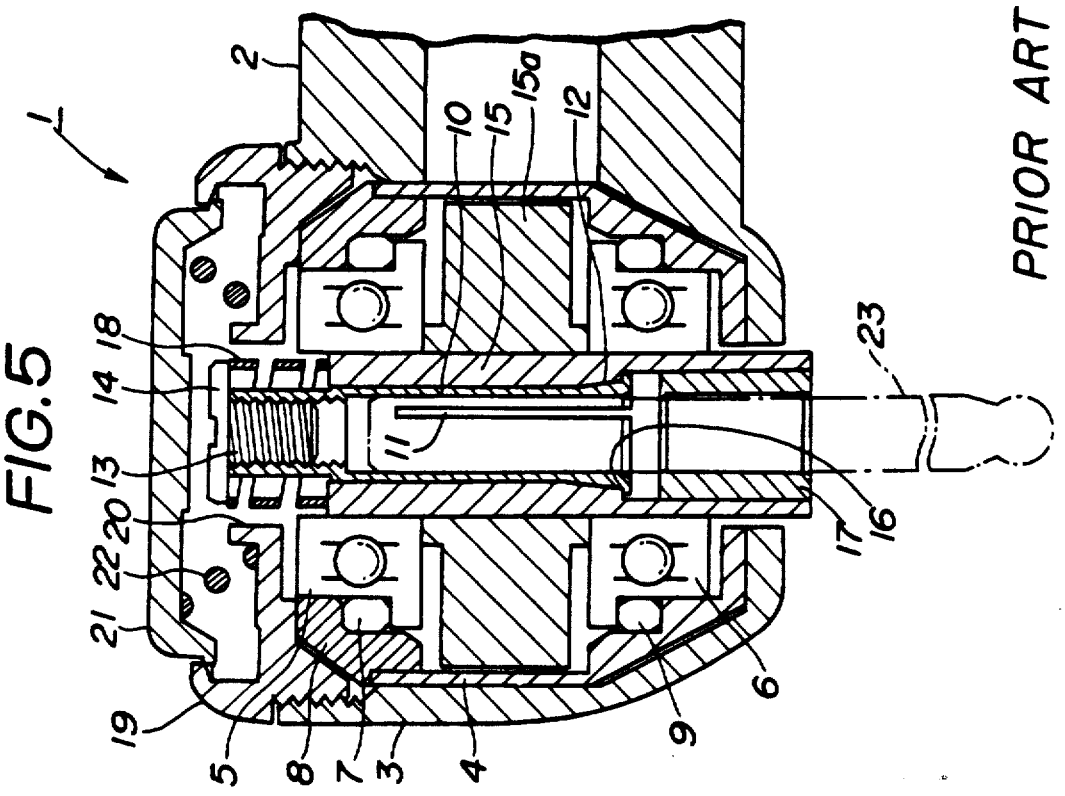
FIG. 5 is a cross-sectional view showing the foremost part of a conventional dental handpiece

By referring to the accompanying drawings, certain perferred embodients of the present invention will be explained in detail. It will be noted that, in FIGS. 1 and 3, parts or components similar to those shown in FIG. 5 are designated by the same reference numerals to avoid redundant description.

Figure 1:
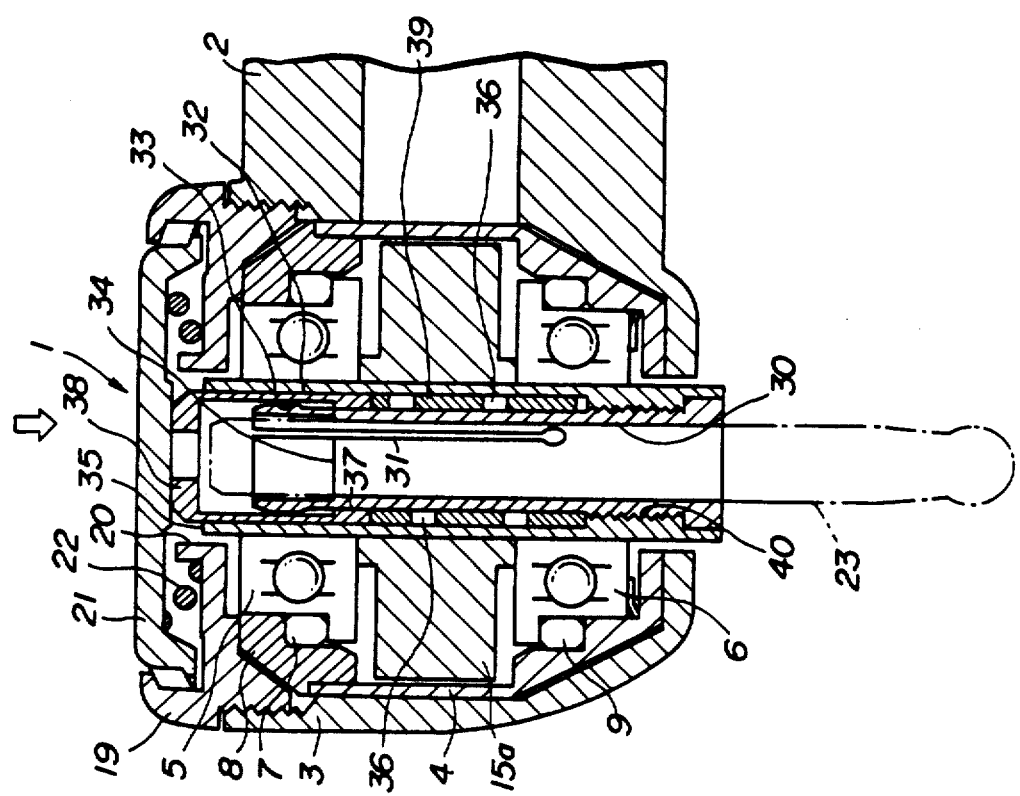
FIG. 1 is a cross-sectional view showing the foremost part of a dental handpiece having therein a chucking device of the present invention.
Figure 3:
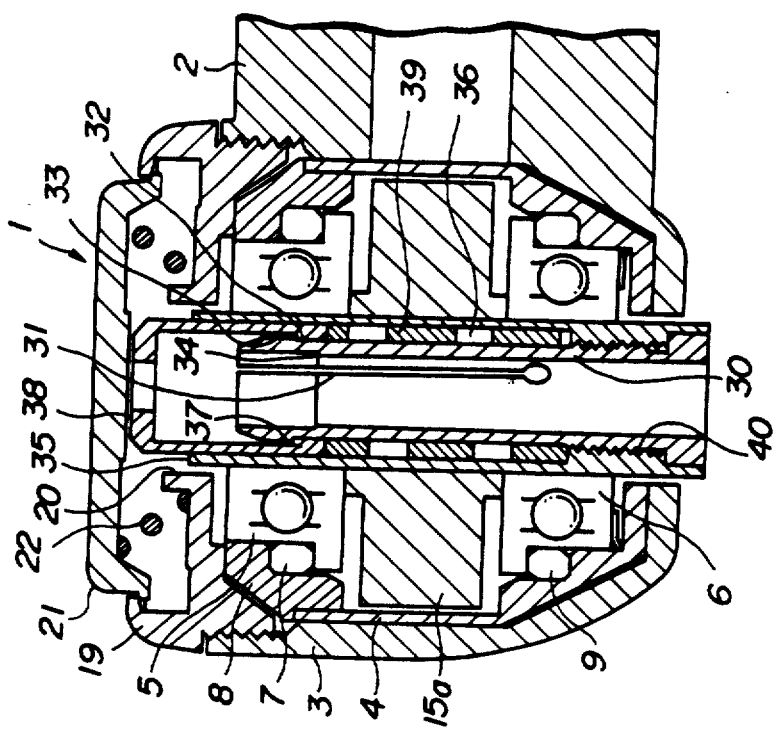
FIG. 3 is a cross-sectional view showing the handpiece of FIG. 1, with the cutting tool shown by a chain-dotted line and with the pushbutton of the handpiece pushed down and the cutting tool inserted into the collect.
Figure 2:
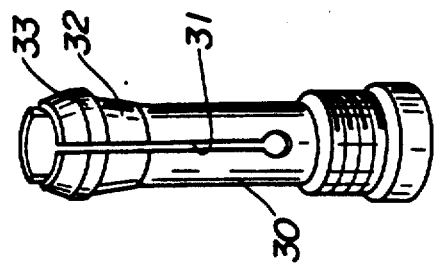
FIG. 2 is a perspective view showing a collet.

In FIG. 1, a tubular collet 30 is formed with a plurality of slits 11 extending axially downwardly from the upper end of the collet 30 to the lower portion of the collet 30, for allowing the collet to be changed in diameter to hold or release the cutting tool 23. As shown in FIG. 2, the outer periphery of the upper end portion of the collet 30 is formed with a tapered surface 32, which is increased in diameter in the upward direction, and an annular step or shoulder 33 in continuation to the tapered surface 32. As shown in FIG. 3, the inner peripheral surface of the collet 30 is formed with a step 34 at a site corresponding to the tapered surface 32, for engaging with and holding substantially the overall circumference of the cutting tool 23.

The collet 30 is accommodated within a rotational sleeve 35 adapted for transmitting rotation to the collet 30 for dental treatment, and has its base portion 40 threadedly attached to the rotational sleeve 35. Between the outer periphery of the collet 30 and the inner periphery of the rotational sleeve 35 is formed an annular space 36 within which a coil spring 39 is mounted for perpetually biasing a locking member 38 upwards from below to bring an annular projection 37 of the locking member 38 into engagement with the step 33 on the outer periphery of the collet 30 to restrict an upward movement of the locking member 38.

The operation of the above described chucking device will be hereinafter explained.

For attaching the cutting tool 23 to the tool head 1, the pushbutton 21 is first pushed down so that the locking member 38 is moved down against the force of the coil spring 39, so that the annular projection 37 of the locking member 38 is moved down in a direction away from the tapered surface 32 of the collet 30. Thus, the collet 30, which has been contracted in diameter as described above, is expanded from its mid height towards its upper end extremity. The cutting tool 23 is introduced in this state at the lower end of the collet 30. The thrusting force applied to the cutting tool 23 is released when the tool 23 reaches the upper end extremity of the locking member 38 which is biased upwards by the coil spring 39. Simultaneously, the finger pressure applied to the pushbutton 21 is released. At this time, the annular projetion 37 of the locking member 38 slides along the tapered surface 32 of the collet 30 in the upward direction of the collet 30, under the repellent force of the coil spring 39, so that the cutting tool 23 is retained in pressure contact with the portion of the inner surface of the collet 30 which is in register with the tapered surface 32. Simultaneously, the edge potion of the step 34 on the inner surface of the collet 30 holds the cutting tool 23 tightly in clamping engagement with the overall periphery of the tool 23. FIG. 3 shows the mounting state of the cutting tool 23. Thus, even if severe vibrations are applied during cutting to the cutting tool 23 and thence to the collet 30, a force in the extracting direction acts on the tool 23, so that the edge portion of the step 34 of the collet 30 nips more and more into the outer periphery of the tool 23 as the tool is about to be moved downwards, to thus prevent inadvertent extraction of the cutting tool 23. When the rotational force is transmitted to a rotor 15a, the rotational sleeve 35 secured to the rotor 15a is driven into rotation to cause rotation of the collet 30 threadedly attached to the sleeve 35 to permit dental treatment by the cutting tool 23 which remains immobilized with respect to the collet 30 as described above.

When detaching the cutting tool 23 during or after dental treatment, the pushbutton 21 is thrust downwards against the force of the coil spring 22 by application of a finger pressure. This causes the locking member 38 to be thrust downwards against the force of the coil spring 39 so that the annular projection 37 of the locking member 38 is slid downwards. By sliding the annular projection 37, the clamping pressure exerted on the upper portion of the collet 30 by the locking member 38 and hence the clamping pressure on the cutting tool 23 by the upper inner periphery of the collet 30 and the step 34 are released. In this manner, the cutting tool 23 may be extracted by hand easily and promptly from the collet 30.

Figure 4C:
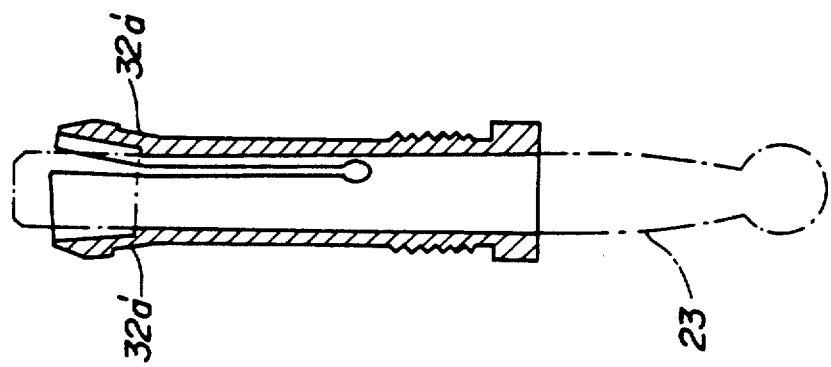
FIG. 4c is a cross-sectional view of the collet of FIG. 4b, with the cutting tool being shown by a chain-dotted line and shown as it is inserted into the inside of the collet.
Figure 4B:
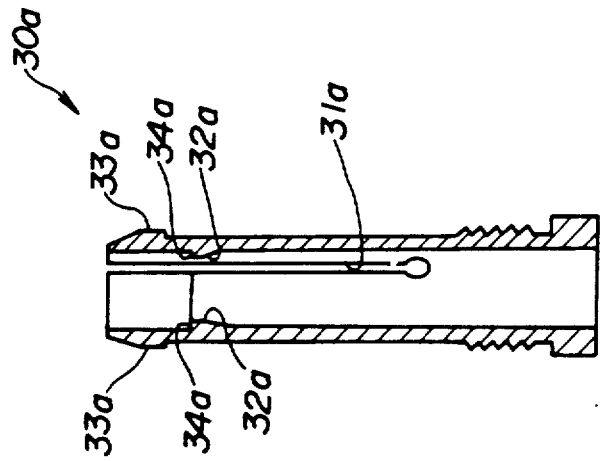
Figure 4A:
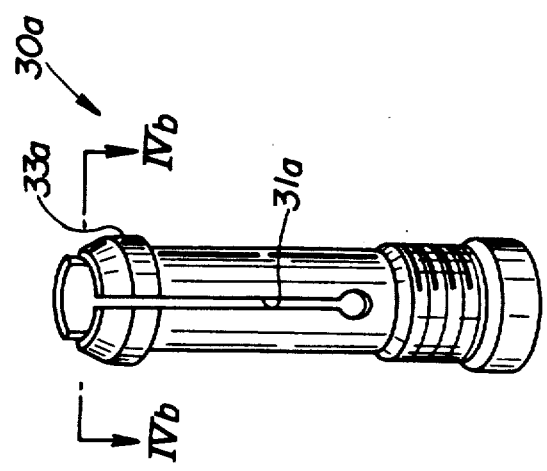
FIG. 4a is a perspective view showing a modification of a collet.

The collet may be constructed as shown in FIGS. 4a and 4b. In these figures, a collet 30a is formed with a plurality of slits 31a extending from the upper end extremity towards a lower portion of the collet 30a, with the exclusion of the lower end portion thereof, to permit the collet diameter to be changed to hold or release the tool 23. An annular shoulder 33a is formed on the upper outer periphery of the collet 30a. A tapered surface 32a increasing in diameter towards below is formed on the upper inner periphery of the collet 30a and a step 34a for abutting on and tightly holding the tool 23 inserted therein over substantially the overall circumference of the tool 23 is formed in continuation to the tapered surface 32a. The collet 30a is accommodated within the rotational sleeve 35 shown in FIGS. 1 and 3 and is threadedly attached at the base portion 40 thereof to the rotational sleeve 35.

The retention operation of the cutting tool 23 is explained for the case in which the above mentioned collet 30a is used. The pushbutton 21 is first thrust downwards to shift the locking member 38 against the force of the coil spring 39 to enable the collet 30a to be expanded. The cutting tool 23 is then introduced at the lower end extremity of the collet 30a until the upper end extremity of the tool 23 abuts on the tapered surface 32a. The collet 30a is expanded in diameter under this thrusting force due to radial expansion at the slits 31a to receive the cutting tool 23 therein. At this time, due to the radial expansion at the slits 31a, a tapered surface 32'a, which is expanded radially progressively along the tool inserting direction as a result of the insertion of the tool 23, is formed on the outer peripheral surface of the collet 30a, as shown in FIG. 4c. When the cutting tool 23 reaches the position of abutting on the upper end of the locking member 38, which is thrust upwards by the coil spring 39, the finger pressure applied to the tool 23 is released. Simultaneously, the finger pressure on the pushbutton 21 is released. The annular projection 37 of the locking member 38 acts on the tapered surface 32'a on the outer periphery of the collet 30a in the direction of reducing the collet diameter, as the locking member 38 is moved upwards under the repulsive force of the coil spring 39, until the projection 37 on the inner periphery of the locking member 38 abuts on the corresponding step 33a on the outer periphery of the collet 30a. Thus, the collet 30a is contracted in diameter to hold the cutting tool 23 in pressure contact with the inner surface of the collet 30a. Simultaneously, the edge portion of the step 34a on the inner periphery of the collet 30a acts to hold the overall periphery of the cutting tool 23 strongly.

In this manner, the holding operation of the cutting tool 23 is performed similarly to the case of the collet 30, in such a manner that, even if the force in the tool extracting direction is applied to the tool 23, the edge portion of the step 34a acts to nip into the outer periphery of the tool 23 to inhibit inadvertent extraction of the tool 23.

When detaching the cutting tool 23, the pushbutton 21 is pressed down to release the pressure applied by the collet 30a to the tool 23 to permit extraction of the tool 23 similarly to the case of the collet 30.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. In a chucking device for a dental handpiece comprising
    a dental tool for performing dental treatment,
    a collet for accommodating said dental tool therein and having a plurality of slits allowing a diameter of the collet to be changed to hold or release the tool, said collet having a tapered surface,
    a rotational sleeve accommodating said collet therein and adapted for transmitting rotation to said collet to permit dental treatment,
    a locking member adapted for being contacted with said tapered surface of said collet for contracting said collet in diameter to hold said dental tool in said collet, and
    thrusting means for thrusting said locking member along an inserting direction of said dental tool,
    the improvement wherein said collet has a tapered surface flared along said inserting direction of said dental tool so that during the operation of attaching said dental tool in position, said locking member thrust by said thrusting means is moved along the tapered surface of said collet along the inserting direction of said tool to contract said collet in diameter to hold said tool in said collet against accidental extraction thereof, and
    wherein during the operation of exchanging said dental tool, said locking member is thrust against a thrusting force of said thrusting means to shift said locking member along said tapered surface of said collet in a direction opposite to the inserting direction of the tool to release the holding of said tool by said collet to thus release said dental tool out of said collet, wherein an annular space is provided between said collet and said rotational sleeve, and wherein said thrusting means is placed within said space.

2. The chucking device for a dental handpiece according to claim 1 wherein said collet has on its outer periphery a tapered surface flared along the inserting direction of said tool.

3. The chucking device for a dental handpiece according to claim 1 wherein said collet has a tapered surface on the inner periphery thereof, said tapered surface being flared in a direction opposite to the inserting direction of said dental tool, and wherein, when said dental tool is inserted into said collet, said collet is expanded in diameter to form a tapered surface on an outer periphery of said collet, said tapered surface being flared along the inserting direction of said dental tool.

4. The chucking device for a dental handpiece according to claim 1 wherein an inner peripheral surface of said collet is formed with a step for holding said dental tool, said step abutting on and holding said dental tool over substantially the entire circumference thereof.

5. The chucking device for a dental handpiece according to any one of claim 1 wherein a projection is formed on an inner end portion of said locking member for pressing the tapered surface on the outer periphery of said collet by said thrusting means to change the diameter of said collet.

6. The chucking device for a dental handpiece according to any one of claim 5 wherein an annular shoulder is formed on the outer periphery of said collet, said annular shoulder being shifted along said tapered surface for engaging with said projection on said locking member.

7. The chucking device for a dental handpiece according to any one of claim 1 wherein said collet is threadedly attached to said rotational sleeve.

8. The chucking device for a dental handpiece according to any one of claim 1 further comprising a pushbutton for thrusting said locking member against a thrusting force of said thrusting means at the time of insertion and exchange of said dental tool.

9. In a chucking device for a dental handpiece comprising in combination:
    a dental tool for performing dental treatment,
    a collet for accommodating said dental tool therein and having a plurality of slits allowing a diameter of the collect to be changed to hold or release the tool, said collet having a tapered surface, a rotational sleeve accommodating said collet therein and adapted for transmitting rotation to said collect to permit dental treatment,
a locking member adapted for being contacted with said tapered surface of said collet for contracting said collet in diameter to hold said dental tool in said collet, and
thrusting means for thrusting said locking member along an inserting direction of said dental tool;
an improvement wherein said collet has a tapered surface flared along said inserting direction of said dental tool so that during the operation of attaching said dental tool in position, said locking member thrust by said thrusting means is moved along the tapered surface of said collet along the inserting direction of said tool to contract said collet in diameter to hold said tool in said collet against accidental extraction thereof, wherein during the operation of exchanging said dental tool, said locking member is thrust against a thrusting force of said thrusting means to shift said locking member along said tapered surface of said collet in a direction opposite to the inserting direction of the tool to release the holding of said tool by said collet to thus release said dental tool out of said collet, and wherein an inner peripheral surface of said collet is formed with a step for holding said dental tool, said step abutting on and holding said dental tool over substantially the entire circumference thereof.

10. The chucking device for a dental handpiece according to any one of claim 1 wherein an annular space is provided between said collet and said rotational sleeve, and wherein said thrusting means is placed within said space.

11. In a chucking device for a dental handpiece comprising in combination:
a dental tool for performing dental treatment,
a collet for accommodating said dental tool therein and having a plurality of slits along a diameter of the collet to be changed to hold or release the tool, said collet having a tapered surface,
a rotational sleeve accommodating said collet therein and adapted for transmitting rotation to said collet to permit dental treatment,
a locking member adapted for being contacted with said tapered surface of said collet for contracting said collet in diameter to hold said dental tool in said collet, and
thrusting means for thrusting said locking member along an inserting direction of said dental tool;
an improvement wherein said collet has a tapered surface flared along said inserting direction of said dental tool so that during the operation of attaching said dental tool in position, said locking member thrust by said thrusting means is moved along the tapered surface of said collet along the inserting direction of said tool to contract said collet in diameter to hold said tool in said collet against accidental extraction thereof, wherein during the operation of exchanging said dental tool, said locking member is thrust against a thrusting force of said thrusting means to shift said locking member along said tapered surface of said collet in a direction opposite to the inserting direction of the tool to release the holding of said tool by said collet to thus release said dental tool out of said collet, wherein a projection is formed on an inner end portion of said locking member for pressing the tapered surface of the outer periphery of said collet by said thrusting means to change the diameter of said collet, and wherein an annular shoulder is formed on the outer periphery of said collet, said annular shoulder being engaged with said projection on said locking member.

* * * * *